US008617529B2

(12) United States Patent
Herrwerth et al.

(10) Patent No.: US 8,617,529 B2
(45) Date of Patent: *Dec. 31, 2013

(54) USE OF ORGANOMODIFIED SILOXANE BLOCK COPOLYMERS AS CARE ACTIVE INGREDIENT FOR THE CARE OF HUMAN OR ANIMAL BODY PARTS

(75) Inventors: Sascha Herrwerth, Essen (DE); Michael Ferenz, Essen (DE); Stefan Busch, Bochum (DE); Jens Barnhusen, Essen (DE); Agnes Kulosa, Herne (DE)

(73) Assignee: Evonik Goldschmidt GmbH, Essen (DE)

( * ) Notice: Subject to any disclaimer, the term of this patent is extended or adjusted under 35 U.S.C. 154(b) by 335 days.

This patent is subject to a terminal disclaimer.

(21) Appl. No.: 12/992,693

(22) PCT Filed: Apr. 15, 2009

(86) PCT No.: PCT/EP2009/054422
§ 371 (c)(1),
(2), (4) Date: Nov. 15, 2010

(87) PCT Pub. No.: WO2009/138305
PCT Pub. Date: Nov. 19, 2009

(65) Prior Publication Data
US 2011/0070175 A1 Mar. 24, 2011

(30) Foreign Application Priority Data

May 15, 2008 (DE) .......................... 10 2008 001 786

(51) Int. Cl.
*A61K 31/74* (2006.01)
*A61K 8/02* (2006.01)
*A61K 31/695* (2006.01)
*A61K 47/00* (2006.01)

(52) U.S. Cl.
USPC .......... 424/78.03; 424/401; 514/63; 514/770; 514/844; 528/25; 528/31

(58) Field of Classification Search
None
See application file for complete search history.

(56) References Cited

U.S. PATENT DOCUMENTS

| 4,853,474 | A * | 8/1989 | Bahr et al. ................. 556/445 |
| 5,281,687 | A | 1/1994 | Busch et al. |
| 5,474,712 | A | 12/1995 | Dotolo et al. |
| 5,879,671 | A | 3/1999 | Halloran et al. |
| 6,242,554 | B1 | 6/2001 | Busch et al. |
| 7,361,777 | B2 | 4/2008 | Herrwerth et al. |
| 7,635,581 | B2 | 12/2009 | Ferenz et al. |
| 2005/0136269 | A1 | 6/2005 | Doehler et al. |
| 2005/0287300 | A1 | 12/2005 | Herrwerth et al. |
| 2006/0041097 | A1 | 2/2006 | Herrwerth et al. |
| 2006/0155089 | A1 | 7/2006 | Ferenz et al. |
| 2006/0155090 | A1 * | 7/2006 | Ferenz ............................ 528/31 |
| 2006/0188455 | A1 | 8/2006 | Ferenz et al. |
| 2006/0188456 | A1 | 8/2006 | Ferenz et al. |
| 2007/0100153 | A1 | 5/2007 | Brueckner et al. |
| 2007/0299231 | A1 | 12/2007 | Doehler et al. |
| 2008/0027202 | A1 | 1/2008 | Ferenz et al. |
| 2008/0216708 | A1 | 9/2008 | Herrwerth et al. |
| 2008/0305065 | A1 | 12/2008 | Ferenz et al. |
| 2009/0062459 | A1 | 3/2009 | Thum et al. |
| 2010/0034765 | A1 | 2/2010 | Herrwerth et al. |
| 2010/0056649 | A1 | 3/2010 | Henning et al. |
| 2010/0056818 | A1 | 3/2010 | Ferenz et al. |
| 2010/0081763 | A1 | 4/2010 | Meyer et al. |
| 2010/0266651 | A1 | 10/2010 | Czech et al. |

FOREIGN PATENT DOCUMENTS

| DE | 3740186 A1 | 1/1989 |
| DE | 3938140 A1 | 8/1991 |
| DE | 4009347 A1 | 9/1991 |
| DE | 4238081 A1 | 7/1993 |
| DE | 4204321 A1 | 8/1993 |
| DE | 4229707 A1 | 3/1994 |
| DE | 4229737 A1 | 3/1994 |
| DE | 4309372 | 9/1994 |
| DE | 4324219 A1 | 1/1995 |
| DE | 196 03 357 A1 | 8/1996 |
| DE | 19855934 A1 | 6/2000 |
| DE | 10327871 A1 | 1/2005 |
| DE | 10 2005 001 040 A1 | 7/2006 |
| DE | 10 2005 001 041 A1 | 7/2006 |
| EP | 0 298 402 | 1/1989 |
| EP | 0666732 B1 | 1/1997 |
| EP | 1 125 574 A2 | 8/2001 |
| EP | 1460098 B1 | 6/2006 |
| EP | 1 679 335 A2 | 7/2006 |
| EP | 1 892 327 A1 | 2/2008 |
| EP | 1892327 * | 2/2008 |
| WO | WO 02/053111 A2 | 7/2002 |
| WO | WO 2009/138305 A1 | 11/2009 |
| WO | WO 2009/138306 A1 | 11/2009 |
| WO | WO 2010/118926 A2 | 10/2010 |

OTHER PUBLICATIONS

Ferenz et al., EP 1892327 machine translation, 2008.*
"Kosmetische Färbemittel"[Cosmetic Colouring Agents] of the Farbstoffkommission der Deutschen Forschungsgemeinschaft [Colorant Commission of the German Research Association], Verlag Chemie, Weinheim, 1984, pp. 81-106.
Finkel, P., et al., "Formulierung Kosmetischer Sonnenschutzmittel", 1996, SÖFW-journal, vol. 122, p. 543.
Abstract of European Patent Publication No. EP 1 679 335, dated Jul. 12, 2006.
International Search Report dated Oct. 1, 2009.
Kollmeier, "Les Copolymeres Polysiloxanes polyethers comme additifs dans les formulations cosmetiques", Parfums, cosmetiques, aromes; 51; 1983; 67-72.

* cited by examiner

*Primary Examiner* — Alton Pryor
(74) *Attorney, Agent, or Firm* — Scully, Scott, Murphy & Presser, P.C.

(57) ABSTRACT

The present invention relates to the use of organomodified siloxane block copolymers as care active ingredient for the care of human or animal body parts.

20 Claims, No Drawings

USE OF ORGANOMODIFIED SILOXANE BLOCK COPOLYMERS AS CARE ACTIVE INGREDIENT FOR THE CARE OF HUMAN OR ANIMAL BODY PARTS

FIELD OF THE INVENTION

The present invention relates to the use of organomodified siloxane block copolymers as care active ingredient for the care of human or animal body parts.

PRIOR ART

Organomodified siloxanes are used in a very wide variety of applications. Their properties can be adjusted, inter alia, through the type of modification, and also by the density of modification.

Thus, for example, it is possible to use allyl polyethers to attach organophilic or nonionic hydrophilic groups to a siloxane backbone. Compounds of this type are used, for example, as polyurethane foam stabilizers, as defoamers in fuels or as additives in paints and coatings.

Thus, for example, DE 102005001041 describes functionalized polyorganosiloxanes and their use as fuel defoamer. The allyl polyethers in the siloxanes described here can, if appropriate, be replaced by altering the synthesis through hydrocarbon radicals.

In general, siloxanes can be linked through reaction with, for example, α-olefins having hydrophobic groups. The silicone waxes obtained in this way serve, for example, as additive in personal care applications.

It is apparent in many fields of application that the effect of the siloxane is decisively dependent on the compatibility with the formulation in question.

Suitable cosmetic emulsifiers are, for example, siloxanes which carry polyethers besides aliphatic groups based on α-olefins. A typical example here is the commercial product ABIL EM 90 from Evonik Goldschmidt GmbH (Germany), which stands out in particular due to excellent stabilization of water-in-oil (W/O) emulsions.

EP 1125574 describes the use of relatively hydrophobic polyethersiloxanes as O/W emulsifiers in which the polyether groups are located on the siloxane backbone in the α-ω-position or terminal position. These structures stand out in particular due to a velvety silky skin feel, which they are able to incorporate into cosmetic emulsions.

U.S. Pat. No. 5,474,712 describes the use of polyether siloxanes according to the prior art in conditioning shampoos for animals.

WO 02/053111 describes the use of silicone polyether block copolymers with $(AB)_n$ structures in aqueous, surface-active body cleaning compositions which have good cosmetic properties specifically for the volume, the combability and the shine of hair.

U.S. Pat. No. 5,879,671 describes the use of aqueous, surface-active body cleaning compositions which comprise mixtures of aminofunctional siloxanes and polyether siloxanes according to the prior art as care active ingredient. These mixtures bring about a long-lasting improvement in the dry and wet combability of hair.

DE 19603357 describes the use of polyether modified MQ resins (polyether dimethylsiloxysilicate) in cosmetic formulations as care active ingredients. These bring about a promotion in shine and retention of curls.

Siloxanes which carry pendent and/or lateral polyether groups are described as care active ingredient for hair and skin in the article "*Les Copolymeres Polysiloxanes polyethers comme additifs dans les formulations cosmetiques*" (Dr. Kollmeier; Parfums, cosmetiques, aromes; 51; 1983; 67-72).

Commercially available care active ingredients based on siloxane are, for example, ABIL B 8842, ABIL B 88183 and ABIL B 8832 (Evonik Goldschmidt GmbH), Belsil DMC 6031, Belsil DMC 6032 and Belsil DMC 6033 (Wacker-Chemie). The commercial product ABIL B 8832 (Evonik Goldschmidt GmbH) is a siloxane modified laterally with polyether groups which is used as care active ingredient for hair and skin in surface-active solutions and care cosmetic formulations. The siloxanes modified laterally with polyether groups are a high-performance class of care active ingredients which bring about a marked conditioning effect for skin and hair from cosmetic formulations. In addition, these lateral siloxanes have foam improving properties. However, the lateral polyether siloxanes have the disadvantage that, even at low use concentrations, they have a considerable viscosity-lowering effect.

Examples of pendent polyether modified siloxanes are ABIL B 8851 and ABIL B 8842 (Evonik Goldschmidt GmbH). From cosmetic, aqueous, surface-active formulations, these bring about a less marked conditioning effect for skin and hair compared to the above-described siloxanes modified laterally with polyether groups. Furthermore, these siloxanes modified in a pendent manner with polyether groups likewise have the disadvantage of having viscosity-lowering properties.

It was therefore an object of the present invention to provide organomodified siloxanes which overcome the aforementioned disadvantages of the prior art as care active ingredient.

DESCRIPTION OF THE INVENTION

Surprisingly, it has been found that the use of organomodified siloxane block copolymers prepared by a process described in claim 1 as care active ingredient for the care of human or animal body parts was able to achieve this object.

The invention therefore provides the use of organomodified siloxane block copolymers prepared by a process described in claim 1 as care active ingredient for the care of human or animal body parts, the formulations themselves and the use of this formulation in, for example, cosmetic applications.

Advantages of the use according to the invention are that the siloxanes, being high-performance care active ingredients, bring about a marked conditioning effect for skin and hair and can be used in aqueous, surface-active formulations, in particular in liquid body cleansing compositions, such as, for example, shower baths and hair shampoos, without giving rise to a significant lowering of the viscosity of the aqueous, surface-active formulation.

It is a further advantage that the siloxanes used are easy to process since they are liquid or are easy to liquefy at room temperature and can be combined with conventional constituents of aqueous, surface-active formulations.

A further advantage is that the use according to the invention as care active ingredient contributes to improved foaming behaviour, increased foam volume and better foam creaminess of the formulations.

A particular advantage of the use according to the invention is the exceptional conditioning effects on skin and hair of the care active ingredient. This conditioning effect on, for example, the skin can prevent a dry, harsh or rough condition of the skin following applications of an aqueous, surface-active formulation, and achieve a pleasant, velvety-silky skin feel.

A further advantage of the invention is that, on account of the reduced viscosity-lowering property, a significant reduction in required thickeners for adjusting the formulation to the desired viscosity is achieved. This permits a simplification of the formulations, which takes into account the resource-preserving aspect.

The invention is described below by way of example without any intention to limit the invention to these exemplary embodiments.

Within the context of the invention, "aqueous formulations" are to be understood as meaning formulations which, based on the total mass, comprise at least 30 mass percent, preferably at least 60 mass percent, particularly preferably at least 80 mass percent, of water.

Within the context of the invention, "aqueous surface-active formulations" are to be understood as meaning formulations which, based on the total mass, comprise less mass percent of oil component than the sum of the mass percents of emulsifier, surfactant and, if appropriate, coemulsifier.

Within the context of the invention, "care active ingredients" are to be understood as meaning organomodified siloxane block copolymers prepared by the process steps according to claim 1, and if appropriate a solvent.

Where ranges, general formulae or compound classes are given below, then these are intended to include not only the corresponding ranges or groups of compounds explicitly mentioned, but also all part ranges and subgroups of compounds which can be obtained by removing individual values (ranges) or compounds. Where documents are cited within the context of the present description, then their contents should in their entirety belong to the disclosure content of the present invention. If, within the context of the present invention, compounds such as, for example, organomodified polysiloxanes, are described which may have different units several times, then these can occur in these compounds in random distribution (random oligomer) or arranged (block oligomer). Data relating to the number of units in such compounds is to be understood as an average value, averaged over all of the corresponding compounds.

Unless stated otherwise, all percentages (%) given are percentages by mass.

The invention provides the use of organomodified siloxane block copolymers prepared by A) addition reaction of organopolysiloxanes of the general formula I

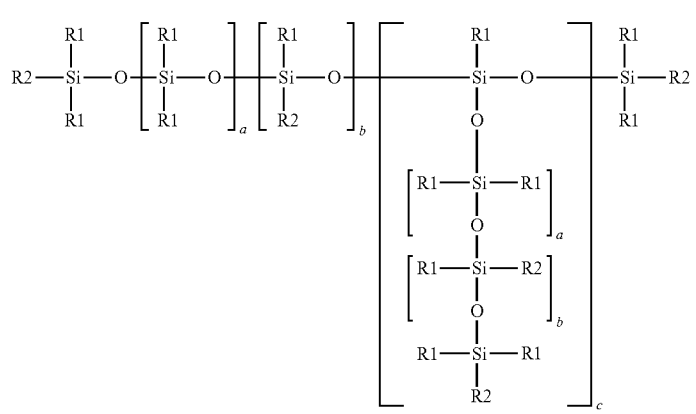

in which $R^1$ are identical or different, branched or unbranched, aliphatic or aromatic hydrocarbon radicals having 1 to 20 carbon atoms, $R^2$ is $R^1$ or H, with the proviso that at least three radicals $R^2$ are H, a is 5 to 500, preferably 10 to 250, in particular 15 to 75, b is 1 to 50, preferably 1 to 20, in particular 3 to 15, c is 0 to 5, preferably 0 to 1, in particular 0, onto siloxanes of the general formula II containing double bonds

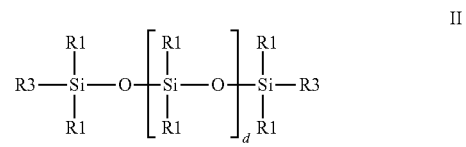

where d is 10 to 1000, preferably 101 to 750, in particular 201 to 500 and $R^3$, independently of one another, are identical or different hydrocarbon radicals having 2 to 12, preferably 2 to 8, in particular 2 carbon atoms and containing at least one double bond, in the presence of platinum or rhodium catalysts, with the proviso that the organopolysiloxanes of the general formula I are present in at least 6-fold molar excess, based on the siloxane of the general formula II containing double bonds, to give a reaction product having Si—H groups and with further reaction of the reaction product in at least one of the stages B) transition-metal-catalysed partial or complete addition of the SiH groups onto alkenyl and/or alkynyl compounds, preferably onto double-bond-containing polyethers and α-olefins, in particular onto allyl polyethers, or C) partial or complete reaction of the Si—H groups remaining after the above reaction(s) in the presence of a catalyst with at least one alcohol, from the group of linear or branched, saturated, mono- or polyunsaturated, aromatic, aliphatic-aromatic, optionally halogen-atom-containing monoalcohols, polyether monoalcohols, polyester monoalcohols, amino alcohols
as care active ingredient for the care of human or animal body parts.

The radicals $R^1$ are preferably identical or different aliphatic or aromatic hydrocarbon radicals having 1 to 20 carbon atoms, further preferably identical or different unbranched, aliphatic or aromatic hydrocarbon radicals having 1 to 9 carbon atoms and particularly preferably methyl, ethyl or phenyl.

The proviso that the SiH-group-carrying organopolysiloxane of the general formula I is present in at least 6-fold molar excess, based on the double bond-containing siloxane of the general formula II, prevents the formation of a network and the formation of highly viscous products resulting. As a rule, the organosiloxanes prepared by one of the two aforementioned processes have viscosities up to 10 000 mPas. A certain fraction of the organosiloxane may be present in the product in the form of a comb-like modified siloxane.

On account of the selected reaction conditions, the double-bond-containing siloxane and the Si-functional siloxane form, in the first stage, a siloxane of the following idealized "H structure" shown in formula III (c=0, $R^1$=Me, $R^2$=R=Me or H):

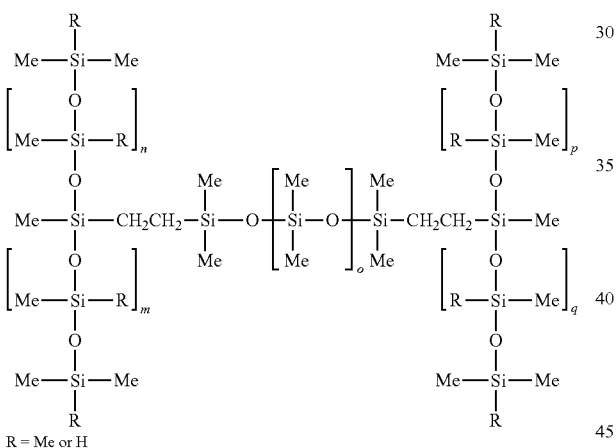

where m, n, o, p and q are positive integers.

This siloxane backbone is retained during subsequent reaction stages. The synthesis of the siloxane polymers can take place with or without solvents. Foaming which may possibly arise can be suppressed through the use of solvents. Suitable solvents are, for example, toluene and cyclohexane.

Effective catalysts which can be used for the first step, the hydrosilylation of the double-bond-containing siloxane A), are Pt- and Rh-containing complexes which are known to the person skilled in the art as hydrosilylation-active catalysts, for example: $H_2PtCl_6$, $Pt[(CH_2CH-Si)_2O]_n$ or $Rh(CO)(C_5H_7O_2)$.

For the addition reaction of the alcohol in process step C) onto the resulting SiH-containing siloxane it is possible to use, for example, Lewis acids, preferably boron-containing Lewis acids. Boron-containing compounds of the catalytic system which may be used are fluorinated and/or nonfluorinated organoboron compounds, in particular those selected from:

$(C_5F_4)(C_6F_5)_2B$; $(C_6F_4)_3B$; $(C_6F_5)BF_2$; $BF(C_6F_5)_2$; $B(C_6F_5)_3$; $BCl_2(C_6F_5)$; $BCl(C_6F_5)_2$; $B(C_6H_5)(C_6F_5)_2$; $B(Ph)_2(C_6F_5)$; $[C_6H_4(mCF_3)]_3B$; $[C_6H_4(pOCF_3)]_3B$; $(C_6F_5)B(OH)_2$; $(C_6F_5)_2BOH$; $(C_6F_5)_2BH$; $(C_6F_5)BH_2$; $(C_7H_{11})B(C_6F_5)_2$; $(C_8H_{14}B)(C_6F_5)$; $(C_6F_5)_2B(OC_2H_5)$; $(C_6F_5)_2B-CH_2CH_2Si(CH_3)$;

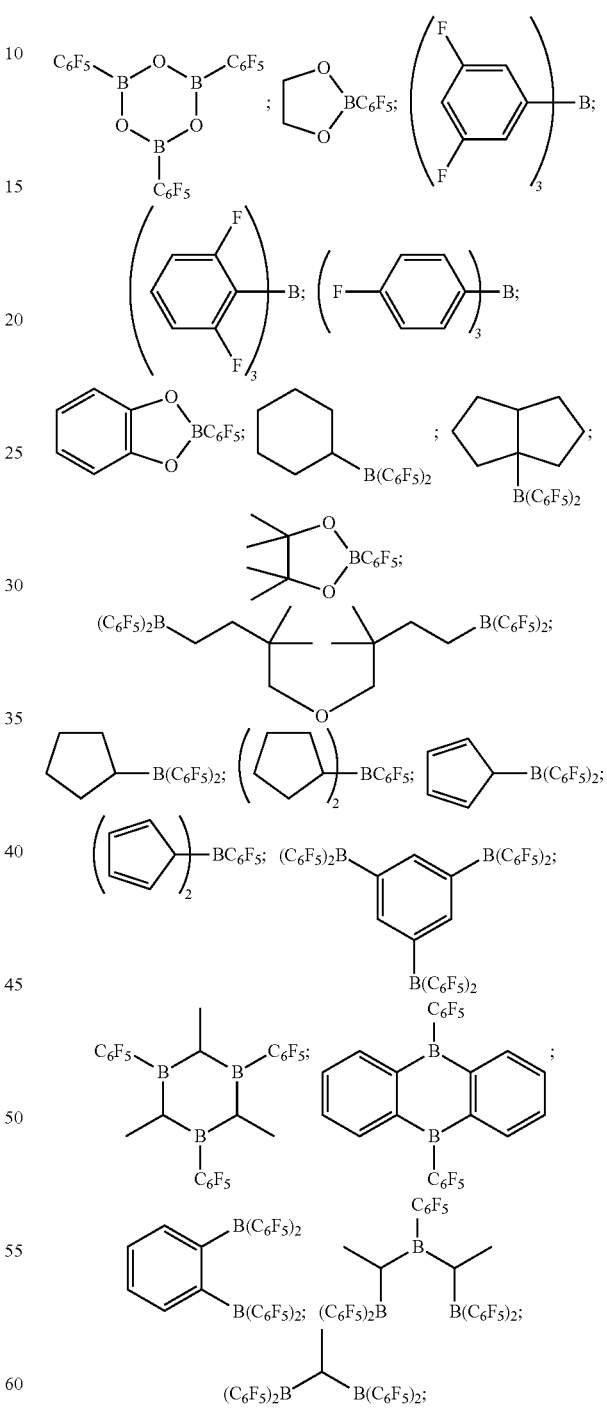

particularly preferably tris(pentafluorotriphenylborane) [CAS No. 1109-15-5], and mixtures of the above catalysts. When using these boron-containing catalysts, it is furthermore possible to use synergistically effective compounds. These include salts or complexes, with cations selected from the group of the salts of elements of the 4th, 6th, 7th and 8th subgroup and also of the 4th main group. Anions of the synergistically active compounds of the catalytic system which may be used are preferably alkoxylates, acid anions, in particular carboxylates, sulphates, nitrates or phosphates, halides, in particular chlorides, oxides or complex ligands, in particular acetyl acetonate or carbonyls.

In addition, DE10312634.1 describes a process for the preparation of organically modified polyorganosiloxanes using a catalytic mixture comprising at least one carboxylic acid and at least one salt of a carboxylic acid by linking hydrogen siloxanes with alcohols. These catalysts can also be used in process step C).

Suitable alcohols are, for example, linear or branched, saturated, mono- or polyunsaturated, aromatic, aliphatic-aromatic monoalcohols or polyalcohols, polyether monoalcohols, polyether polyalcohols, polyester monoalcohols, polyester polyalcohols, amino alcohols, in particular N-alkyl-, arylamino-EO-, -PO-alcohols (EO stands for the polyethylene oxide radical, PO for the polypropylene oxide radical), N-alkyl- or arylamino alcohols, and mixtures thereof. Polyether monoalcohols are particularly suitable.

Effective catalysts which can be used for the transition-metal-catalysed addition of the SiH groups of the siloxane prepared in the first step onto CC multiple bonds in process step B) are the known hydrosilylation catalysts, for example: $H_2PtCl_6$, $Pt[(CH_2CH-Si)_2O]_n$ or $Rh(CO)(C_5H_7O_2)$.

Suitable alkenyl/alkynyl compounds are, for example, polyethers with multiple bonds, for example butanediol alkoxylates or allyl-functional polyethers, olefins, ethene, ethyne, propene, 1-butene, 1-hexene, 1-dodecene, 1-hexadecene, allyl alcohol, 1-hexenol, styrene, eugenol, allyl phenol, methyl undecylenate. Of particular suitability are polyethers with double bonds, in particular allyl-functional polyethers.

A further constituent of the invention is care formulations comprising the care active ingredient according to the invention.

Preferably, the care formulations comprise from 0.01 mass percent to 20 mass percent, preferably 0.05 mass percent to 10 mass percent, particularly preferably 0.1 mass percent to 3 mass percent of care active ingredient, based on the total mass of the care formulation.

The care formulations are likewise preferably aqueous, particularly preferably aqueous, surface-active formulations.

These care formulations are preferably cosmetic, dermatological or pharmaceutical formulations.

These may be, for example: shower baths and shower gels, bath formulations, liquid soaps and shampoos, skin masks, shaving foams, hair conditioners, leave-in conditioners and styling products for hair.

The care formulations according to the invention can comprise, for example, at least one additional component selected from the group of emollients,
emulsifiers and surfactants,
thickeners/viscosity regulators/stabilizers,
UV photoprotective filters,
antioxidants and vitamins,
hydrotropes (or polyols),
solids and fillers,
film-formers,
pearlescent additives,
deodorant and antiperspirant active ingredients,
insect repellents,
self-tanning agents,
preservatives,
conditioners,
perfumes,
dyes,
biogenic active ingredients,
care additives,
superfatting agents,
solvents.

Emollients which can be used are all cosmetic oils, in particular mono- or diesters of linear and/or branched mono- and/or dicarboxylic acids having 2 to 44 carbon atoms with linear and/or branched saturated or unsaturated alcohols having 1 to 22 carbon atoms. It is likewise possible to use the esterification products of aliphatic, difunctional alcohols having 2 to 36 carbon atoms with monofunctional aliphatic carboxylic acids having 1 to 22 carbon atoms. Also suitable are long-chain aryl acid esters, such as, for example, esters of benzoic acid, e.g. benzoic acid esters of linear or branched, saturated or unsaturated alcohols having 1 to 22 carbon atoms, or else isostearyl benzoate or octyldodecyl benzoate. Further monoesters suitable as emollients and oil components are, for example, the methyl esters and isopropyl esters of fatty acids having 12 to 22 carbon atoms, such as, for example, methyl laurate, methyl stearate, methyl oleate, methyl erucate, isopropyl palmitate, isopropyl myristate, isopropyl stearate, isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, and esters which are obtainable from technical-grade aliphatic alcohol cuts and technical-grade, aliphatic carboxylic acid mixtures, e.g. esters of unsaturated fatty alcohols, having 12 to 22 carbon atoms and saturated and unsaturated fatty acids having 12 to 22 carbon atoms, as are accessible from animal and vegetable fats. Also suitable, however, are naturally occurring monoester and/or wax ester mixtures, as are present, for example in jojoba oil or in sperm oil. Suitable dicarboxylic acid esters are, for example, di-n-butyl adipate, di-n-butyl sebacate, di(2-ethylhexyl) adipate, di(2-hexyldecyl) succinate, diisotridecyl azelate. Suitable diol esters are, for example, ethylene glycol dioleate, ethylene glycol diisotridecanoate, propylene glycol di(2-ethylhexanoate), butanediol diisostearate, butanediol dicaprylate/caprate and neopentyl glycol dicaprylate. Further fatty acid esters which can be used as emollients are, for example, $C_{12}$-$_{15}$ alkyl benzoate, dicaprylyl carbonate, diethylhexyl carbonate. Emollients and oil components which can likewise be used are longer-chain triglycerides, i.e. triple esters of glycerol with three acid molecules, of which at least one is relatively long-chain. By way of example, mention may be made here of fatty acid triglycerides; examples of such which may be used are natural, vegetable oils, e.g. olive oil, sunflower oil, soybean oil, peanut oil, rapeseed oil, almond oil, sesame oil, avocado oil, castor oil, cocoa butter, palm oil, but also the liquid fractions of coconut oil or of palm kernel oil, and also animal oils, such as, for example, shark liver oil, cod liver oil, whale oil, beef tallow and butter fat, waxes such as beeswax, carnauba palm wax, spermaceti, lanolin and neat's-foot oil, the liquid fractions of beef tallow and also synthetic triglycerides of capryl/capric acid mixtures, triglycerides of technical-grade oleic acid, triglycerides with isostearic acid, or from palmitic acid/oleic acid mixtures as emollients and oil components. Furthermore, hydrocarbons, in particular also liquid paraffins and isoparaffins, can be used. Examples of hydrocarbons which can be used are paraffin oil, isohexadecane, polydecene, vaseline, Paraffinum perliquidum, squalane, ceresin. Furthermore, it is also possible to use linear or branched fatty alcohols such as oleyl alcohol or octyldodecanol, and also fatty alcohol ethers such as dicaprylyl ether. Suitable silicone oils and silicone waxes are, for example, polydimethylsiloxanes, cyclomethylsiloxanes, and also aryl- or alkyl- or alkoxy-substituted polymethylsiloxanes or cyclomethylsiloxanes. Suitable further oil bodies are, for example, Guerbet alcohols based on fatty alcohols having 6 to 18, preferably 8 to 10, carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, esters of linear $C_6$-$C_{22}$-fatty acids with branched $C_8$-$C_{18}$-alcohols, in particular 2-ethylhexanol or isononanol, esters of branched $C_6$-$C_{13}$-carboxylic acids with branched alcohols, in particular 2-ethylhexanol or isononanol, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, vegetable oils, branched primary alcohols, substituted cyclohexanes, linear $C_6$-$C_{22}$-fatty alcohol carbonates, Guerbet carbonates, esters of benzoic acid with linear and/or branched $C_6$-$C_{22}$-alcohols (e.g. Finsolv™ TN), dialkyl ethers, ring-opening products of epoxidized fatty acid esters with polyols, silicone oils and/or aliphatic or naphthenic hydrocarbons.

Emulsifiers or surfactants which may be used are nonionic, anionic, cationic or amphoteric surfactants.

Nonionogenic emulsifiers or surfactants which can be used are compounds from at least one of the following groups:
addition products of from 2 to 100 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
$C_{12/18}$-fatty acid mono- and diesters of addition products of from 1 to 100 mol of ethylene oxide onto glycerol,
glycerol mono- and diesters and sorbitan mono- and diesters of saturated and unsaturated fatty acids having 6 to 22 carbon atoms and ethylene oxide addition products thereof, alkyl mono- and oligoglycosides having 8 to 22 carbon atoms in the alkyl radical and ethylene oxide addition products thereof,
addition products of from 2 to 200 mol of ethylene oxide onto castor oil and/or hydrogenated castor oil,
partial esters based on linear, branched, unsaturated or saturated $C_6$-$C_{22}$-fatty acids, ricinoleic acid, and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose),
mono-, di- and trialkylphosphates, and mono-, di- and/or tri-PEG alkyl phosphates and salts thereof,
polysiloxane-polyether copolymers (dimethicone copolyols), such as, for example PEG/PPG-20/6 dimethicone, PEG/PPG-20/20 dimethicone, bis-PEG/PPG-20/20 dimethicone, PEG-12 or PEG-14 dimethicone, PEG/PPG-14/4 or 4/12 or 20/20 or 18/18 or 17/18 or 15/15,
polysiloxane-polyalkyl-polyether copolymers and corresponding derivatives, such as, for example, lauryl or cetyl dimethicone copolyols, in particular cetyl PEG/PPG-10/1 dimethicone (ABIL® EM 90 (Evonik)),
mixed esters of pentaerythritol, fatty acids, citric acid and fatty alcohol as in DE 11 65 574 and/or mixed esters of fatty acids having 6 to 22 carbon atoms, methylglucose and polyols, such as, for example, glycerol or polyglycerol, citric acid esters, such as, for example, glyceryl stearate citrate, glyceryl oleate citrate and dilauryl citrate.

Anionic emulsifiers or surfactants can contain water-solubilizing anionic groups, such as, for example, a carboxylate, sulphate, sulphonate or phosphate group and a lipophilic radical. Skin-compatible anionic surfactants are known to the person skilled in the art in large numbers and are commercially available. Here, these may be alkyl sulphates or alkyl phosphates in the form of their alkali metal, ammonium or alkanolammonium salts, alkyl ether sulphates, alkyl ether carboxylates, acyl sarcosinates, and sulphosuccinates and acyl glutamates in the form of their alkali metal or ammonium salts.

Cationic emulsifiers and surfactants can also be added. Those which can be used are, in particular, quaternary ammonium compounds, in particular those provided with at least one linear and/or branched, saturated or unsaturated alkyl chain having 8 to 22 carbon atoms, such as, for example, alkyltrimethylammonium halides, such as, for example, cetyltrimethylammonium chloride or bromide or behenyltrimethylammonium chloride, but also dialkyldimethylammonium halides, such as, for example, distearyldimethylammonium chloride.

Furthermore, monoalkylamidoquats such as, for example, palmitamidopropyltrimethylammonium chloride or corresponding dialkylamidoquats, can be used.

Furthermore, readily biodegradable quaternary ester compounds can be used; these may be quaternized fatty acid esters based on mono-, di- or triethanolamine. Furthermore, alkylguanidinium salts can be added as cationic emulsifiers.

Typical examples of mild, i.e. particularly skin-compatible, surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, ether carboxylic acids, alkyl oligoglucosides, fatty acid glucamides, alkylamidobetaines and/or protein fatty acid condensates, the latter for example based on wheat proteins.

Furthermore, it is possible to use amphoteric surfactants, such as, for example, betaines, amphoacetates or amphopropionates, thus, for example, substances such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and also cocoacylaminoethyl hydroxyethylcarboxymethyl glycinate.

Of the ampholytic surfactants, it is possible to use those surface-active compounds which, apart from a C8/18-alkyl or -acyl group in the molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Further examples of ampholytic surfactants are N-cocoalkylaminopropionate, cocoacylaminoethylaminopropionate and C12/18-acylsarcosine.

Suitable thickeners are, for example, polysaccharides, in particular xanthan gum, guar-guar, agar agar, alginates and tyloses, carboxymethylcellulose and hydroxyethylcellulose, also relatively high molecular weight polyethylene glycol mono- and diesters of fatty acids, polyacrylates (e.g. Carbopols™ or Synthalens™), polyacrylamides, polyvinyl alcohol and polyvinylpyrrolidone, surfactants such as, for example, ethoxylated fatty acid glycerides, esters of fatty acids with polyols, such as, for example, pentaerythritol or trimethylolpropane, fatty alcohol ethoxylates with a narrowed homologue distribution or alkyl oligoglucosides, and also electrolytes such as sodium chloride and ammonium chloride.

Suitable thickeners for thickening oil phases are all thickeners known to the person skilled in the art. In particular, mention is to be made here of waxes, such as hydrogenated castor wax, beeswax or microwax. Furthermore, inorganic thickeners can also be used, such as silica, alumina or sheet silicates (e.g. hectorite, laponite, saponite). In this connection, these inorganic oil phase thickeners may be hydrophobically modified. For the thickening/stabilization of water-in-oil emulsions, in particular aerosils, sheet silicates and/or metal salts of fatty acids, such as, for example, zinc stearate, can be used here.

Viscosity regulators for aqueous surfactant systems which may be present are, for example NaCl, low molecular weight non-ionic surfactants, such as cocoamide DEA/MEA and laureth-3, or polymeric, high molecular weight, associative, highly ethoxylated fat derivatives, such as PEG-200 hydrogenated glyceryl palmate.

UV photoprotective filters which can be used are, for example, organic substances which are able to absorb ultraviolet rays and which give off the absorbed energy again in the form of longer-wave radiation, e.g. heat. UVB filters may be oil-soluble or water-soluble. Examples of oil-soluble UVB photoprotective filters are:

3-benzylidenecamphor and derivatives thereof, e.g. 3-(4-methylbenzylidene)camphor, 4-aminobenzoic acid derivatives, such as, for example, 2-ethylhexyl 4-(dimethylamino)benzoate and amyl 4-(dimethylamino)benzoate, esters of cinnamic acid, such as 2-ethylhexyl 4-methoxycinnamate, isopentyl 4-methoxycinnamate, 2-ethylhexyl 2-cyano-3-phenylcinnamate (octocrylene), esters of salicylic acid, such as, for example, 2-ethylhexyl salicylate, 4-isopropylbenzyl salicylate, homomethyl salicylate, derivatives of benzophenone, such as, for example, 2-hydroxy-4-methoxybenzophenone, 2-hydroxy-4-methoxy-4'-methylbenzophenone, 2,2'-dihydroxy-4-methoxybenzophenone, esters of benzalmalonic acid, such as, for example, di-2-ethylhexyl 4-methoxybenzmalonate, triazine derivatives, such as, for example, 2,4,6-trianilino-(p-carbo-2'-ethyl-1'-hexyloxy)-1,3,5-triazine and octyltriazone, propane-1,3-diones, such as, for example, 1-(4-tert-butylphenyl)-3-(4'-methoxyphenyl)propane-1,3-dione.

Suitable water-soluble UVB photoprotective filters are:
2-phenylbenzimidazole-5-sulphonic acid and the alkali metal, alkaline earth metal, ammonium, alkylammonium, alkanolammonium and glucammonium salts thereof,
sulphonic acid derivatives of benzophenone, such as, for example, 2-hydroxy-4-methoxybenzophenone-5-sulphonic acid and its salts,
sulphonic acid derivatives of 3-benzylidenecamphor, such as, for example, 4-(2-oxo-3-bornylidenemethyl)benzenesulphonic acid and 2-methyl-5-(2-oxo-3-bornylidene) sulphonic acid and salts thereof.

Suitable typical UVA photoprotective filters are in particular derivatives of benzoylmethane, such as, for example, 1-(4'-tert-butylphenyl)-3-(4'-methoxyphenyl)propane-1,3-dione or 1-phenyl-3-(4'-isopropylphenyl)propane-1,3-dione. The UV-A and UV-B filters can of course also be used in mixtures.

Besides the specified soluble substances, insoluble pigments, namely finely disperse metal oxides or salts are also suitable for this purpose, such as, for example, titanium dioxide, zinc oxide, iron oxide, aluminium oxide, cerium oxide, zirconium oxide, silicates (talc), barium sulphate and zinc stearate. The particles here should have an average diameter of less than 100 nm, e.g. between 5 and 50 nm and in particular between 15 and 30 nm. They can have a spherical shape, although it is also possible to use those particles which have an ellipsoidal shape or a shape which deviates in some other way from the spherical form. A relatively new class of photoprotective filters are micronized organic pigments, such as, for example, 2,2'-methylenebis{6-(2H-benzotriazol-2-yl)-4-(1,1,3,3-tetramethylbutyl)phenol} with a particle size of <200 nm, which is obtainable, for example, as 50% strength aqueous dispersion.

Further suitable UV photoprotective filters can be found in the overview by P. Finkel in SÖFW-Journal 122, 543 (1996). Besides the two aforementioned groups of primary UV photoprotective filters, it is also possible to use secondary photoprotective agents of the antioxidant type which interrupt the photochemical reaction chain which is triggered when UV radiation penetrates into the skin.

Antioxidants and vitamins which can be used are, for example, superoxide-dismutase, tocopherol (vitamin E), tocopherol sorbate, tocopherol acetate, other esters of tocopherol, dibutylhydroxytoluene and ascorbic acid (vitamin C) and its salts, and also derivatives thereof (e.g. magnesium ascorbyl phosphate, sodium ascorbyl phosphate, ascorbyl sorbate), ascorbyl esters of fatty acids, butylated hydroxybenzoic acid and its salts, peroxides, such as, for example, hydrogen peroxide, perborates, thioglycolates, persulphate salts, 6-hydroxy-2,5,7,8-tetramethylchroman-2-carboxylic acid (TROLOX®), gallic acid and its alkyl esters, uric acid and its salts and alkyl esters, sorbic acid and its salts, lipoic acid, ferulic acid, amines (e.g. N,N-diethylhydroxylamine, aminoguanidines), sulphydryl compounds (e.g. glutathione), dihydroxyfumaric acid and its salts, glycine pidolate, arginine pilolate, nordihydroguaiaretic acid, bioflavonoids, curcumin, lysine, L-methionine, proline, superoxide dismutase, silymarin, tea extract, grapefruit peel/pip extract, melanin, rosemary extract, thiooctanoic acid, resveratrol, oxyresveratrol, etc.

Hydrotropes which can be used for improving the flow behaviour and the application properties are, for example, ethanol, isopropyl alcohol or polyols. Polyols which are suitable here can have 2 to 15 carbon atoms and at least 2 hydroxyl groups.

Typical Examples are:
glycerol alkylene glycols, such as, for example, ethylene glycol, diethylene glycol, propylene glycol, butylene glycol, hexylene glycol, and polyethylene glycols with an average molecular weight of from 100 to 1000 daltons, technical-grade oligoglycerol mixtures with a degree of self-condensation of from 1.5 to 10, such as, for example, technical-grade diglycerol mixtures with a diglycerol content of from 40 to 50% by weight, methylol compounds, such as in particular trimethylolethane, trimethylolpropane, trimethylolbutane, pentaerythritol and dipentaerythritol, lower alkyl glucosides, in particular those with 1 to 4 carbon atoms in the alkyl radical, such as, for example, methyl and butyl glucoside, sugar alcohols having 5 to 12 carbon atoms, such as, for example, sorbitol or mannitol, sugars having 5 to 12 carbon atoms, such as, for example, glucose or sucrose, amino sugars, such as, for example, glucamine.

Solids which can be used are, for example, iron oxide pigments, titanium dioxide or zinc oxide particles and those additionally specified under "UV protectants". Furthermore, it is also possible to use particles which lead to special sensory effects, such as, for example, nylon-12, boron nitride, polymer particles such as, for example, polyacrylate or polymethyl acrylate particles or silicone elastomers. Fillers which can be used include starch and starch derivatives, such as tapioca starch, distarch phosphate, aluminium starch or sodium starch, octenyl succinate, and pigments which have neither primarily a UV filter effect nor a colouring effect, for example Aerosils® (CAS No. 7631-86-9).

Examples of film formers which can be used, for example, for improving the water resistance are: polyurethanes, dimethicones, copolyol, polyacrylates or PVP/VA copolymer (PVP=polyvinylpyrrolidone, VA=vinyl acetate). Fat-soluble film formers which can be used are: e.g. polymers based on polyvinylpyrrolidone (PVP), copolymers of polyvinylpyrrolidone, PVP/hexadecene copolymer or the PVP/eicosene copolymer.

Pearlescence additives which can be used are, for example, glycol distearates or PEG-3 distearate.

Suitable deodorant active ingredients are, for example, odour concealers such as the customary perfume constituents, odour absorbers, for example the sheet silicates described in the patent laid-open specification DE 40 09 347, of these, in particular montmorillonite, kaolinite, illite, beidelite, nontronite, saponite, hectorite, bentonite, smectite, or also, for example, zinc salts of ricinoleic acid. Antimicrobial agents are likewise suitable for being incorporated. Antimicrobial substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbonilide, quaternary ammonium compounds, clove oil, mint oil, thyme oil, triethyl citrate, farnesol (3,7,11-trimethyl-2,6,10-dodecatrien-1-ol), ethylhexyl glyceryl ether, polyglyceryl-3 caprylate (TEGO® Cosmo P813, Evonik), and the effective agents described in the patent laid-open specifications DE 198 55 934, DE 37 40 186, DE 39 38 140, DE 42 04 321, DE 42 29 707, DE 42 29 737, DE 42 38 081, DE 43 09 372, DE 43 24 219 and EP 666 732.

Antiperspirant active ingredients which may be used are astringents, for example basic aluminium chlorides such as aluminium chlorohydrate ("ACH") and aluminium zirconium glycine salts ("ZAG").

Insect repellents which may be used are, for example, N,N-diethyl-m-toluamide, 1,2-pentanediol or Insect Repellent 3535.

Self-tanning agents which can be used are, for example, dihydroxyacetone and erythrulose.

Preservatives which can be used are, for example, mixtures of one or more alkyl paraben esters with phenoxyethanol. The alkyl paraben esters may be methyl paraben, ethyl paraben, propyl paraben and/or butyl paraben. Instead of phenoxyethanol, it is also possible to use other alcohols, such as, for example, benzyl alcohol or ethanol. Moreover, it is also possible to use other customary preservatives such as, for example, sorbic acid or benzoic acid, salicylic acid, 2-bromo-2-nitropropane-1,3-diol, chloroacetamide, diazolidinylurea, DMDM hydantoin, iodopropynyl butylcarbamate, sodium hydroxymethylglycinates, methylisothiazoline, chloromethylisothiazoline, ethylhexylglycerol or caprylyl glycol.

Conditioning agents which can be used are, for example, organic quaternary compounds, such as cetrimonium chloride, dicetyldimonium chloride, behentrimonium chloride, distearyldimonium chloride, behentrimonium methosulphate, distearoylethyldimonium chloride, palmitamidopropyltrimonium chloride, guar hydroxypropyltrimonium chloride, hydroxypropylguar, hydroxypropyltrimonium chloride, or quaternium-80 or else amine derivatives such as, for example, aminopropyldimethicones or stearamidopropyldimethylamines.

Perfumes which can be used are natural or synthetic odorants or mixtures thereof. Natural odorants are extracts from flowers (lily, lavender, rose, jasmine, neroli, ylang-ylang), stems and leaves (geranium, patchouli, petitgrain), fruits (anise, coriander, caraway, juniper), fruit peels (bergamot, lemon, orange), roots, (maize, angelica, celery, cardamon, costus, iris, thyme), needles and branches (spruce, fir, pine, dwarf-pine), resins and balsams (galbanum, elemi, benzoin, myrrh, olibanum, opoponax). Animal raw materials are also suitable, such as, for example, civet and castoreum. Typical synthetic odorant compounds are products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include primarily the terpenes and balsams. It is possible to use mixtures of different odorants which together produce a pleasant scent note. Essential oils of low volatility, which are mostly used as aroma components, are also suitable as perfumes, e.g. sage oil, camomile oil, clove oil, Melissa oil, mint oil, cinnamon leaf oil, linden blossom oil, juniperberry oil, vetiver oil, olibanum oil, galbanum oil, labolanum oil and lavandin oil. It is also possible to use bergamot oil, dihydromyrcenol, lilial, lyral, citronellol, phenylethyl alcohol, α-hexylcinnamaldehyde, geraniol, benzyl acetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-E-Super, Fixolide NP, Evernyl, Iraldein gamma, phenylacetic acid, geranyl acetate, benzyl acetate, rose oxide, romillat, irotyl and floramat alone or in mixtures.

Dyes which can be used are the substances approved and suitable for cosmetic purposes, as are listed, for example, in the publication "Cosmetic Colorants" of the Dyes Commission of the German Research Society, Verlag Chemie, Weinheim, 1984, pp. 81 to 106. These dyes are usually used in concentrations of from 0.001 to 0.1% by weight, based on the total mixture.

Biogenic active ingredients are to be understood as meaning, for example, tocopherol, tocopherol acetate, tocopherol palmitate, ascorbic acid, polyphenols, deoxyribonucleic acid, coenzyme Q10, retinol, bisabolol, allantoin, panthenol, phytantriol, AHA acids, amino acids, hyaluronic acid, alpha-hydroxy acids, isoflavones, polyglutamic acid, creatine (and creatine derivatives), guanidine (and guanidine derivatives), ceramides, phytosphingosine (and phytosphingosine derivatives), sphingosine (and sphingosine derivatives), pseudoceramides, essential oils, peptides, protein hydrolysates, plant extracts, sphinolipids, idebenone, liquorice extract, glycyrrhizidine and idebenone, scleroglucan, β-glucan, santalbic acid and vitamin complexes. Examples of plant extracts are horsechestnut extract, camomile extract, rosemary extract, blackcurrant and redcurrant extract, birch extract, rosehip extract, algae extract, green tea extract, aloe extract, ginseng extract, ginkgo extract, grapefruit extract, calendula extract, camphor, thyme extract, mangosteen extract, cystus extract, Terminalia arjuna extract, oat extract, oregano extract, raspberry extract, strawberry extract, etc.

The biogenic active ingredients can also include the so-called barrier lipids, examples of which being ceramides, phytosphingosine and derivatives, sphingosine and derivatives, sphinganine and derivatives, pseudoceramides, phospholipids, lysophospholipids, cholesterol and derivatives, cholesteryl ester, free fatty acids, lanolin and derivatives, squalane, squalene and related substances. Within the context of the invention, the biogenic active ingredients also include anti-acne, such as, for example, benzyl peroxide, phytosphingosine and derivatives, niacinamide hydroxybenzoate, nicotinaldehyde, retinol acid and derivatives, salicylic acid and derivatives, citronellic acid etc., and anti-cellulite, such as, for example, xanthine compounds such as caffeine, theophylline, theobromine and aminophylline, carnitine, carnosine, salicyloyl phytosphingosine, phytosphingosines, santalbic acid etc., as well as antidandruff agents such as, for example, salicylic acid and derivatives, zinc pyrithione, selenium sulphide, sulphur, cyclopiroxolamine, bifonazole, climbazole, octopirox and actirox etc., as well as astringents, such as, for example, alcohol, aluminium derivatives, gallic acid, pyridoxine salicylate, zinc salts, such as, for example, zinc sulphate, acetate, chloride, lactate, zirconium chlorohydrates etc. Bleaches such as kojic acid, arbutin, vitamin C and derivatives, hydroquinone, turmeric oil, creatinine, sphingolipids, niacinamide, etc. may likewise be included in the biogenic active ingredients.

Care additives which may be present are, for example, ethoxylated glycerol fatty acid esters, such as, for example, PEG-7 glycerol cocoate, or cationic polymers, such as, for example, polyquaternium-7 or polyglycerol esters.

Superfatting agents which can be used are substances such as, for example, lanolin and lecithin, and also polyethoxylated or acylated lanolin and lecithin derivatives, polyol fatty acid esters, monoglycerides and fatty acid alkanolamides, with the latter simultaneously serving as foam stabilizers.

Solvents which can be used are, for example, aliphatic alcohols such as ethanol, propanol or 1,3-propanediol, cyclic carbonates, such as ethylene carbonate, propylene carbonate, glycerol carbonate, esters of mono- or polycarboxylic acids such as ethyl acetate, ethyl lactate, dimethyl adipate and diethyl adipate, propylene glycol, dipropylene glycol, glycerol, glycerol carbonate or water.

The care formulations preferably consist of the care active ingredient according to the invention, solvent and optionally a preservative. In this connection, the preferred solvents are alcohols, alkoxylated fatty alcohols, polyethers and water.

Care formulations according to the invention can be used as skincare product, face care product, head care product, body care product, intimate care product, foot care product, hair care product, nail care product, dental care product or mouth care product.

Care formulations according to the invention can be used in the form of an emulsion, a suspension, a solution, a cream, an ointment, a paste, a gel, an aerosol, a spray, a cleansing product, a make-up or sunscreen preparation or a facial toner.

Care formulations corresponding to the present invention have a conditioning effect on skin and hair.

The invention therefore provides the use of formulation according to the invention for the conditioning of skin and/or hair; the invention further provides the use of formulation according to the invention for imparting a pleasant velvety silky skin feel and for avoiding a dry or harsh condition of the skin, the invention yet further provides the use of formulation according to the invention for improving at least one property of the hair selected from the group: combability, softness, ability to be shaped, manageability, detanglability, volume, shine.

Care formulations according to the invention reduce the roughness of stressed skin. The invention therefore further provides the use of the formulations according to the invention for reducing skin roughness.

The present invention is described by way of example in the examples listed below, without any intention to limit the invention, the scope of application of which arises from the entire description and the claims, to the embodiments specified in the examples.

EXAMPLES

Organomodified Siloxane Block Copolymer 1/Care Active Ingredient 1 (According to the Invention)

141 g of an SiH-functional siloxane of the general empirical formula $Me_3SiO—(SiMe_2O)_{28}(SiMeHO)_{10}SiMe_3$ were mixed with 108 g of a divinylsiloxane of the general formula $CH_2\!\!=\!\!CH—SiMe_2O—(SiMe_2O)_{349}—SiMe_2\text{-}CH\!\!=\!\!CH_2$ and heated to 105° C. A platinum catalyst was then added and the mixture was stirred for 30 minutes. 397 g of a polyether of the general formula $CH_2\!\!=\!\!CH—CH_2—O—(CH_2CH_2O)_{12}Me$ were then added. Stirring was then carried out for a further 6 h at 125° C.

Organomodified Siloxane Block Copolymer 2/Care Active Ingredient 2 (According to the Invention)

84 g of an SiH-functional siloxane of the general empirical formula $Me_3SiO—(SiMe_2O)_{28}(SiMeHO)_{10}SiMe_3$ were mixed with 56 g of a divinylsiloxane of the general formula $CH_2\!\!=\!\!CH—SiMe_2O—(SiMe_2)_{349}—SiMe_2\text{-}CH\!\!=\!\!CH_2$ and heated to 110° C. An Rh catalyst was then added and the mixture was stirred for 30 minutes. The mixture was then cooled to 90° C. and a Pt catalyst and 602 g of a polyether of the general formula $CH_2\!\!=\!\!CH—CH_2O(CH_2CH_2O)_{24}(CH_2CH(CH_3)O)_4Me$ were added. The mixture was stirred for a further 2 h at 120° C.

Organomodified Siloxane Block Copolymer 3/Care Active Ingredient 3 (According to the Invention)

171 g of an SiH-functional siloxane of the general empirical formula $Me_3SiO—(SiMe_2O)_{28}(SiMeHO)_{10}SiMe_3$ were mixed with 131 g of a divinylsiloxane of the general formula $CH_2\!\!=\!\!CH—SiMe_2O—(SiMe_2O)_{349}—SiMe_2\text{-}CH\!\!=\!\!CH_2$ and 200 g of a propoxylated myristyl alcohol (PPG-3 myristyl ether) and heated to 105° C. A platinum catalyst was then added and the mixture was stirred for 30 minutes. 490 g of a polyether of the general formula $CH_2\!\!=\!\!CH—CH_2O(CH_2CH_2O)_{12}Me$ were then added. The mixture was stirred for a further 6 h at 125° C.

Organomodified Siloxane Block Copolymer 4/Care Active Ingredient 4 (According to the Invention)

216 g of an SiH-functional siloxane of the general empirical formula $Me_3SiO—(SiMe_2O)_{28}(SiMeHO)_{10}SiMe_3$ were mixed with 165 g of a divinylsiloxane of the general formula $CH_2=CH-SiMe_2O-(SiMe_2O)_{349}SiMe_2-CH=CH_2$ and heated to 105° C. A platinum catalyst was then added and the mixture was stirred for 30 minutes. 845 g of a polyether of the general formula $CH_2=CH-CH_2O(CH_2CH_2O)_{12}Me$ were then added. The mixture was then stirred for a further 3 h at 125° C.

Comparative Examples 5 to 7

Not According to the Invention, for Distinguishing from the Prior Art

Comparative Example 5

Not According to the Invention 490 g of an allyl polyether of the general formula $CH_2=CH-CH_2-O-(C_2H_4O)_{21}-(C_3H_6O)_{22}-H$ were initially introduced into a reaction flask, heated to 100° C. and treated with 10 ppm of a Pt catalyst. 382 g of an SiH siloxane of the general formula $H(CH_3)_2SiO-[(CH_3)_2SiO]_{60}-Si(CH_3)_2H$ were then slowly metered in. This mixture was stirred for a further 3 h.

Comparative Example 6

Not According to the Invention 280 g of an allyl polyether of the general formula $CH_2=CH-CH_2-O-(C_2H_4O)_{13}-(C_3H_6O)_4-H$ were initially introduced in a reaction flask, heated to 100° C. and treated with 10 ppm of a Pt catalyst. 97 g of an SiH siloxane of general formula $(CH_3)_3SiO-[(CH_3)_2SiO]_{20}-[(CH_3)_2HSiO]_5-Si(CH_3)_3$ were then slowly metered in. This mixture was stirred for a further 4 h.

Comparative Example 7

Not According to the Invention 266 g of an allyl polyether of the general formula $CH_2=CH-CH_2-O-(C_2H_4O)_{20}-(C_3H_6O)_5-H$ were initially introduced in a reaction flask, heated to 100° C. and treated with 10 ppm of a Pt catalyst. 200 g of an SiH siloxane of the general formula $(CH_3)_3SiO-[(CH_3)_2SiO]_{75}-[(CH_3)_2 HSiO]_5-Si(CH_3)_3$ were then slowly metered in. This mixture was stirred for a further 4 h.

The structures of the Comparative Examples 5 to 7 correspond to the general formula:

$R_1(CH_3)_2SiO-[(CH_3)_2SiO]_n-[(CH_3)R_2SiO]_m-Si(CH_3)_2R_1$ where: $R_1$, $R_2=CH_3$ or a polyether ("PE") of the type:

$-(CH_2)_w-O-(C_2H_4O)_x-(C_3H_6O)_y-R_3$ where $R_3=H$

TABLE 1

Comparative Examples 5 to 7.

| Comparative Example | n | m | $R_1$ | $R_2$ | $R_3$ | w | x | y |
|---|---|---|---|---|---|---|---|---|
| 5 | 60 | 0 | PE | — | H | 3 | 21 | 22 |
| 6 | 20 | 5 | Me | PE | H | 3 | 13 | 4 |
| 7 | 75 | 5 | Me | PE | H | 3 | 20 | 5 |

Comparative Example 5 corresponds to a lateral polyethersiloxane according to the prior art.

Comparative Examples 6 and 7 correspond to pendent polyethersiloxanes according to the prior art.

Application Examples

All of the concentrations given in the application examples are in percentages by weight. To prepare the formulations, customary formulation processes known to the person skilled in the art were used.

Viscosity Effect:

To investigate the viscosity effects of the organomodified siloxane block copolymers 1 to 4 according to the invention and of the polyethersiloxanes according to the prior art 5 to 7, these compounds were tested in a surfactant system with a customary thickener Antil 171, Evonik Goldschmidt GmbH (INCI: PEG-18 Glyceryl Oleate/Cocoate).

The formulations were stored for 24 hours at 25° C. following preparation and then the viscosity was measured using a Brookfield viscometer (Brookfield LVF, spindle 3, 5 rpm) at 25° C.

A formulation without addition of a polyether siloxane is used as control formulation 0a.

The results of the formulations 1a, 2a, 3a and 4a with the organomodified siloxane block copolymer care active ingredients 1 to 4 according to the invention, of the formulations C5a, C6a and C7a with the polyethersiloxanes according to the prior art 5 to 7 and of the control formulation 0a without polyethersiloxane (test formulation) are summarized in Table 2.

TABLE 2

Measured viscosities upon using PEG-18 Glyceryl Oleate/Cocoate (Antil 171, Evonik Goldschmidt GmbH) for thickening the aqueous, surface-active formulation.

| | Formulation examples | | | | | | | |
|---|---|---|---|---|---|---|---|---|
| | 0a | 1a | 2a | 3a | 4a | C5a | C6a | C7a |
| Texapon NSO ®, 28% strength, Cognis (INCI: Sodium Laureth Sulfate) | 32% | 32% | 32% | 32% | 32% | 32% | 32% | 32% |
| TEGO Betain F 50 ®, 38% strength, Evonik Goldschmidt GmbH (INCI: Cocamidopropyl Betaine) | 8% | 8% | 8% | 8% | 8% | 8% | 8% | 8% |

TABLE 2-continued

Measured viscosities upon using PEG-18 Glyceryl Oleate/Cocoate (Antil 171, Evonik Goldschmidt GmbH) for thickening the aqueous, surface-active formulation.

| | Formulation examples | | | | | | | |
|---|---|---|---|---|---|---|---|---|
| | 0a | 1a | 2a | 3a | 4a | C5a | C6a | C7a |
| Antil 171, Evonik Goldschmidt GmbH (INCI: PEG-18 Glyceryl Oleate/Cocoate) | 4.4% | 4.4% | 4.4% | 4.4% | 4.4% | 4.4% | 4.4% | 4.4% |
| Water, demineralized | | | | ad 100.0 | | | | |
| Organomodified siloxane block copolymer 1 (according to the invention) | | 0.5% | | | | | | |
| Organomodified siloxane block copolymer 2 (according to the invention) | | | 0.5% | | | | | |
| Organomodified siloxane block copolymer 3 (according to the invention) | | | | 0.5% | | | | |
| Organomodified siloxane block copolymer 4 (according to the invention) | | | | | 0.5% | | | |
| Comparative Example 5 | | | | | | 0.5% | | |
| Comparative Example 6 | | | | | | | 0.5% | |
| Comparative Example 7 | | | | | | | | 0.5% |
| Viscosity [mPas] (after 24 hours) | 4800 | 4650 | 4750 | 5200 | 5000 | 900 | 2600 | 3000 |

From the measurement results in Tab. 2 it is evident that in the case of the aqueous, surface-active formulations according to the invention, no significant reduction in the viscosities compared to the control formulation 0a takes place. In the case of the Comparative Formulations C5a, C6a and C7a, according to the prior art, on the other hand, there is a considerable decrease in the viscosity compared to the control formulation 0a.

2.) Testing the Conditioning of Skin (Skincare Performance) and Foam Properties by Means of a Handwashing Test:

To evaluate the conditioning of skin (skincare performance) and the foam properties of the organomodified siloxane block copolymer care active ingredients 1 to 4 according to the invention in aqueous, surface-active formulations, sensory handwashing tests compared to the Comparative Examples 5 to 7 according to the prior art were carried out.

Comparative Examples 5 to 7 are widespread in the industry as care active ingredients and regarded as highly effective care active ingredients in aqueous, surface-active formulations.

A group consisting of 10 trained test subjects washed their hands in a defined manner and evaluated foam properties and skin feel using a grading scale from 1 (poor) to 5 (very good). The products used were in each case tested in a standardized surfactant formulation (Table 3).

A formulation without addition of a polyether siloxane is used as control formulation 0b.

TABLE 3

Test formulations for handwashing test.

| | Formulation examples | | | | | | | |
|---|---|---|---|---|---|---|---|---|
| | 0b | 1b | 2b | 3b | 4b | C5b | C6b | C7b |
| Texapon NSO ®, 28% strength, Cognis (INCI: Sodium Laureth Sulfate) | 32% | 32% | 32% | 32% | 32% | 32% | 32% | 32% |
| TEGO Betain F 50 ®, 38% strength, Evonik Goldschmidt GmbH (INCI: Cocamidopropyl Betaine) | 8% | 8% | 8% | 8% | 8% | 8% | 8% | 8% |
| NaCl | 2% | 2% | 2% | 2% | 2% | 2% | 2% | 2% |
| Water, demineralized | | | | ad 100.0 | | | | |
| Organomodified siloxane block copolymer 1 (according to the invention) | | 0.5% | | | | | | |

TABLE 3-continued

Test formulations for handwashing test.

| Formulation examples | 0b | 1b | 2b | 3b | 4b | C5b | C6b | C7b |
|---|---|---|---|---|---|---|---|---|
| Organomodified siloxane block copolymer 2 (according to the invention) | | 0.5% | | | | | | |
| Organomodified siloxane block copolymer 3 (according to the invention) | | | 0.5% | | | | | |
| Organomodified siloxane block copolymer 4 (according to the invention) | | | | 0.5% | | | | |
| Comparison compound 5 | | | | | | 0.5% | | |
| Comparison compound 6 | | | | | | | 0.5% | |
| Comparison compound 7 | | | | | | | | 0.5% |

The sensory test results are summarized in Table 4.

TABLE 4

Results of the handwashing test

| Test formulation | 0b | 1b | 2b | 3b | 4b | C5b | C6b | C7b |
|---|---|---|---|---|---|---|---|---|
| Foaming behaviour | 3.0 | 3.5 | 3.3 | 3.1 | 3.3 | 3.1 | 3.0 | 3.1 |
| Foam volume | 2.8 | 3.0 | 3.0 | 2.8 | 2.9 | 2.7 | 2.8 | 2.6 |
| Foam creaminess | 2.3 | 3.1 | 2.9 | 2.7 | 2.8 | 2.6 | 2.5 | 2.6 |
| Skin feel during washing | 2.8 | 3.8 | 3.6 | 3.6 | 3.8 | 3.5 | 3.1 | 3.3 |
| Skin smoothness | 1.4 | 2.6 | 2.7 | 2.8 | 2.5 | 2.4 | 1.9 | 2.0 |
| Skin softness | 2.0 | 2.7 | 2.6 | 2.6 | 2.8 | 2.6 | 2.4 | 2.3 |
| Skin smoothness after 3 min | 2.6 | 3.5 | 3.4 | 3.4 | 3.4 | 3.3 | 3.0 | 3.1 |
| Skin softness after 3 min | 2.5 | 3.5 | 3.6 | 3.5 | 3.7 | 3.3 | 2.9 | 3.1 |

The results of the handwashing test are shown in Table 4. From the measurement results it is evident that the formulations 1b to 4b according to the invention with use of the organomodified siloxane block copolymers 1 to 4 according to the invention bring about better skin smoothness and skin softness 3 minutes after application and a superior skin feel during washing compared to the comparison formulations C5b, C6b and C7b according to the prior art. Skin smoothness and skin softness directly after application in the case of the formulations 1b to 4b according to the invention are also at the same level or superior to the measurement values in the case of the comparison formulations C5b, C6b and C7b. In addition, the measurement values reveal that the lateral polyethersiloxane (comparison formulation C5b) is superior to the pendent polyethersiloxanes (comparison formulations C6b and C7b) with regard to skin conditioning.

Against this background, the results of the formulations 1b to 4b according to the invention are to be deemed very good. Furthermore, it is evident from the measurement values that the organomodified siloxane block copolymers 1 to 4 according to the invention in the formulations 1b to 4b bring about an improvement in the foam properties, specifically the foam creaminess.

3.) Testing the Conditioning of Hair by Means of a Sensory Test:

For the application-related assessment of the conditioning of hair, the organomodified siloxane block copolymers 1 and 2 according to the invention and the comparison product 5 were used in simple cosmetic formulations (shampoo and hair conditioner).

The application properties upon use in a shampoo were investigated in the following formulations:

TABLE 5

Shampoo formulations for testing the hair-conditioning properties.

| Formulation examples | 0c | 1c | 2c | C5c |
|---|---|---|---|---|
| Texapon NSO ®, 28% strength, Cognis (INCI: Sodium Laureth Sulfate) | 32% | 32% | 32% | 32% |
| TEGO ® Betain F 50, 38% strength, Evonik Goldschmidt GmbH (INCI: Cocamidopropyl Betaine) | 8% | 8% | 8% | 8% |
| Jaguar 162, Rhodia (INCI: Guar Hydroxypropyl trimonium Chloride) (cationic polymer for improving the effectiveness of conditioners) | 0.3% | 0.3% | 0.3% | 0.3% |
| Water, demineralized | ad 100.0 | | | |
| Citric acid | ad pH 6.0 ± 0.3 | | | |
| Organomodified siloxane block copolymer 1 (according to the invention) | | 0.5% | | |
| Organomodified siloxane block copolymer 2 (according to the invention) | | | 0.5% | |
| Comparison compound 5 | | | | 0.5% |

To evaluate the properties of the shampoo formulation, no after treatment with a conditioner was carried out in the course of the test.

The application properties upon use in hair conditioners were investigated in the following formulations:

TABLE 6

Hair conditioner formulations for testing the hair-conditioning properties.

| Formulation examples | 0d | 1d | 2d | C5d |
|---|---|---|---|---|
| TEGINACID ®C, Evonik Goldschmidt GmbH (INCI: Ceteareth-25) | 0.5% | 0.5% | 0.5% | 0.5% |
| TEGO ®Alkanol 16, Evonik Goldschmidt GmbH (INCI: Cetyl Alcohol) | 4% | 4% | 4% | 4% |
| VARISOFT ® 300, 30% strength, Evonik Goldschmidt GmbH (INCI: Cetrimonium Chloride) | 3.3% | 3.3% | 3.3% | 3.3% |
| Water, demineralized | ad 100.0 | | | |
| Citric acid | ad pH 4.0 ± 0.3 | | | |

TABLE 6-continued

Hair conditioner formulations for testing
the hair-conditioning properties.

| Formulation examples | 0d | 1d | 2d | C5d |
|---|---|---|---|---|
| Organomodified siloxane block copolymer 1 (according to the invention) | | 0.5% | | |
| Organomodified siloxane block copolymer 2 (according to the invention) | | | 0.5% | |
| Comparison compound 5 | | | | 0.5% |

In the case of the property testing of hair conditioners, the hair is pretreated using a shampoo which does not contain conditioning agents.

For the application-related assessment, hair tresses which are used for sensory tests are predamaged in a standardized manner by a permanent wave treatment and a bleaching treatment. For this, customary styling products are used. The test procedure, the base materials used and also the details of the assessment criteria are described in DE 103 27 871.

Standardized treatment of predamaged hair tresses with conditioning samples:

The predamaged hair tresses, as described above, are treated as follows with the shampoo described above or the conditioning rinse described above:

The hair tresses are wetted under running warm water. The excess water is gently squeezed out by hand, then the shampoo is applied and gently worked into the hair (1 ml/hair tress (2 g)). After a residence time of 1 min, the hair is rinsed for 1 min.

Optionally, the rinse is applied directly afterwards and gently worked into the hair (1 ml/hair tress (2 g)). After a residence time of 1 min, the hair is rinsed for 1 min.

Prior to the sensory assessment, the hair is dried in the air at 50% atmospheric humidity and 25° C. for at least 12 h.
Assessment Criteria:

The sensory evaluations are made using grades which are awarded on a scale from 1 to 5, with 1 being the poorest evaluation and 5 being the best evaluation. The individual test criteria are each given their own evaluation.

The test criteria are: wet combability, wet feel, dry combability, dry feel, appearance/shine.

The table below compares the results of the sensory assessment of the treatment of the hair tresses carried out as described above with the formulations 1c and 2c according to the invention, the comparison formulation C5c and the control formulation 0c (placebo without test substance).

TABLE 7

Results of the conditioning of hair from shampoo formulation

| | Wet combability | Wet feel | Dry combability | Dry feel | Shine |
|---|---|---|---|---|---|
| Formulation 1c according to the invention | 3.8 | 3.8 | 4.3 | 4.3 | 3.9 |
| Formulation 2c according to the invention | 3.5 | 3.6 | 4.4 | 4.3 | 4.1 |
| Comparison formulation C5c (not according to the invention) | 3.0 | 3.0 | 3.0 | 3.5 | 3.0 |

TABLE 7-continued

Results of the conditioning of hair from shampoo formulation

| | Wet combability | Wet feel | Dry combability | Dry feel | Shine |
|---|---|---|---|---|---|
| Control formulation 0c (placebo) | 2.3 | 2.5 | 2.8 | 3.3 | 2.3 |

The results surprisingly show that the formulations 1c and 2c according to the invention with the organomodified siloxane block copolymers 1 and 2 receive significantly better evaluations than the comparison formulation C5c with the comparison compound 5 according to the prior art. The good evaluation of the shine properties of all of the formulations according to the invention is particularly clearly emphasized.

TABLE 8

Results of the conditioning of hair from hair conditioner formulations

| | Wet combability | Wet feel | Dry combability | Dry feel | Shine |
|---|---|---|---|---|---|
| Formulation 1d according to the invention | 4.7 | 5.0 | 4.8 | 4.7 | 4.6 |
| Formulation 2d according to the invention | 4.9 | 4.8 | 4.7 | 4.9 | 4.5 |
| Comparison formulation C5d (not according to the invention) | 4.5 | 4.2 | 4.5 | 4.3 | 3.8 |
| Control formulation 0d | 3.8 | 3.9 | 4.0 | 3.8 | 2.9 |

In the hair conditioner application too, the formulations 1d and 2d according to the invention with the organomodified siloxane block copolymers 1 and 2 exhibit very good cosmetic evaluations in the sensory assessment. Here, the already very good properties of the comparison formulation C5d with the comparison compound 5 were yet further increased through the formulations 1d and 2d according to the invention with organomodified siloxane block copolymers 1 and 2.

A significantly better evaluation is also achieved in the case of the shine through the use of the formulations 1d and 2d according to the invention.

Further Formulation Examples

These examples are intended to show that the organomodified siloxane block copolymers according to the invention can be used in a large number of cosmetic formulations.

| Conditioning shampoo | |
|---|---|
| TEXAPON ® NSO, Cognis, 28% strength (INCI: Sodium Laureth Sulfate) | 25% |
| Perfume | 0.3% |
| Organomodified siloxane block copolymer 1 (according to the invention) | 0.5% |
| ABIL ® Quat 3272, Evonik Goldschmidt GmbH (INCI: Quaternium-80) | 0.5% |
| PLANTACARE ® 1200 UP, Cognis 50% (INCI: Lauryl Glycoside) | 4.25% |
| Water | 54.7% |
| TEGO ® Betain F 50, Evonik Goldschmidt GmbH, 38% strength (INCI: Cocamidopropyl Betaine) | 14.25% |

Conditioning shampoo

| | |
|---|---|
| ANTIL ® 171, Evonik Goldschmidt GmbH (INCI: PEG-18 Glyceryl Oleate/Cocoate) | 0.5% |

Moisturizing body wash

| | |
|---|---|
| TEXAPON ® NSO, Cognis, 28% strength (INCI: Sodium Laureth Sulfate) | 30% |
| TEGOSOFT ® PC 31, Evonik Goldschmidt GmbH (INCI: Polyglyceryl-3 Caprate) | 0.5% |
| Organomodified siloxane block copolymer 1 (according to the invention) | 0.3% |
| Perfume | 0.3% |
| Water | 54.1% |
| TEGOCEL ® HPM 4000, Evonik Goldschmidt GmbH (INCI: Hydroxypropyl Methylcellulose) | 0.3% |
| REWOTERIC ® AM C, Evonik Goldschmidt GmbH, 32% strength (INCI: Sodium Cocoamphoacetate) | 10% |
| Citric Acid Monohydrate | 0.5% |
| REWODERM ® LI S 80, Evonik Goldschmidt GmbH (INCI: PEG-200 Hydrogenated Glyceryl Palmate; PEG-7 Glyceryl Cocoate) | 2% |
| TEGO ® Pearl N 300, Evonik Goldschmidt GmbH (INCI: Glycol Distearate; Laureth-4; Cocamidopropyl Betaine) | 2% |

Body cleansing foam

| | |
|---|---|
| TEXAPON ® NSO, Cognis, 28% strength (INCI: Sodium Laureth Sulfate) | 14% |
| Perfume | 0.3% |
| Organomodified siloxane block copolymer 2 (according to the invention) | 0.5% |
| REWOTERIC ® AM C, Evonik Goldschmidt GmbH, 32% strength (INCI: Sodium Cocoamphoacetate) | 8% |
| Water | 75.2% |
| TEGOCEL ® HPM 50, Evonik Goldschmidt GmbH (INCI: Hydroxypropyl Methylcellulose) | 0.5% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1% |
| Citric Acid Monohydrate | 0.5% |

Mild shower bath

| | |
|---|---|
| TEXAPON ® NSO, Cognis, 28% strength (INCI: Sodium Laureth Sulfate) | 27% |
| REWOPOL ® SB FA 30, Evonik Goldschmidt GmbH, 40% strength (INCI: Disodium Laureth Sulfosuccinate) | 12% |
| TEGOSOFT ® LSE 65 K SOFT, Evonik Goldschmidt GmbH (INCI: Sucrose Cocoate) | 2% |
| Water | 39% |
| REWOTERIC ® AM C, Evonik Goldschmidt GmbH, 32% strength (INCI: Sodium Cocoamphoacetate) | 13% |
| Organomodified siloxane block copolymer 3 (according to the invention) | 0.5% |
| Citric acid (30% in water) | 3% |
| ANTIL ® 171 Evonik Goldschmidt GmbH (INCI: PEG-18 Glyceryl Oleate/Cocoate) | 1.5% |
| TEGO ® Pearl N 300 Evonik Goldschmidt GmbH (INCI: Glycol Distearate; Laureth-4; Cocamidopropyl Betaine) | 2% |

Hair conditioner

| | | |
|---|---|---|
| A | Water | 93.75% |
| | Propylene glycol | 1% |
| | Citric acid monohydrate | q.s. |
| B | TEGO ® Alkanol 16, Evonik Goldschmidt GmbH (INCI: Cetyl alcohol) | 3% |
| | VARISOFT ® PATC, Evonik Goldschmidt GmbH (INCI: Palmitamidopropyltrimonium Chloride) | 1.75% |
| | Organomodified siloxane block copolymer 1 (according to the invention) | 0.5% |
| C | Perfume, preservative | q.s. |

Hair repair leave-in conditioner spray

| | |
|---|---|
| TAGAT ® CH-40, Evonik Goldschmidt GmbH (INCI: PEG-40 Hydrogenated Castor Oil) | 2% |
| Ceramide VI, Evonik Goldschmidt GmbH (INCI: Ceramide 6 II) | 0.05% |
| Perfume | 0.2% |
| Water | 89.75% |
| Organomodified siloxane block copolymer 4 (according to the invention) | 0.5% |
| Organomodified siloxane block copolymer (according to the invention) | 1.5% |
| LACTIL ® Evonik Goldschmidt GmbH (INCI: Sodium Lactate; Sodium PCA; Glycine; Fructose; Urea; Niacinamide; Inositol; Sodium benzoate; Lactic Acid) | 2% |
| TEGO ® Betain F 50 Evonik Goldschmidt GmbH 38% (INCI: Cocamidopropyl Betaine) | 2% |
| Citric Acid (10% in water) | 2% |

Leave-in conditioning mousse

| | |
|---|---|
| Organomodified siloxane block copolymer 1 (according to the invention) | 0.5% |
| ABIL ® B 88183, Evonik Goldschmidt GmbH (INCI: PEG/PPG-20/6 Dimethicone) | 0.4% |
| TAGAT ® CH-40 (INCI: PEG-40 Hydrogenated Castor Oil) | 0.5% |
| Perfume | 0.2% |
| TEGO ® Betain 810, Evonik Goldschmidt GmbH, 38% strength (INCI: Capryl/Capramidopropyl Betaine) | 4% |
| Water | 93.5% |
| Panthenol | 0.2% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 0.3% |
| Citric Acid (30% in water) | 0.4% |

Creamy shaving foam

| | | |
|---|---|---|
| A | Water | 50% |
| | Coconut fatty acid | 1.4% |
| | Monoethanolamine | 1.3% |
| | Myristic acid | 3.5% |
| B | TEGOSOFT ® LSE 65 K Evonik Goldschmidt (INCI: Sucrose Cocoate) | 2% |
| C | TEGO ® Betain 810 Evonik Goldschmidt (INCI: Capryl/Capramidopropyl Betaine) | 7.6% |
| | Glycerol | 5% |
| | Organomodified siloxane block copolymer 1 (according to the invention) | 1.7% |
| | Perfume | 0.3% |
| | Water | 26.5% |

| Creamy shaving foam | |
|---|---|
| TEGOCEL ® HPM 50 Evonik Goldschmidt (INCI: Hydroxypropyl Methylcellulose) | 0.7% |

The invention claimed is:

1. A method of preparing an organomodified siloxane block copolymer, said method comprising:

A) incorporating at least one organopolysiloxane of general formula I

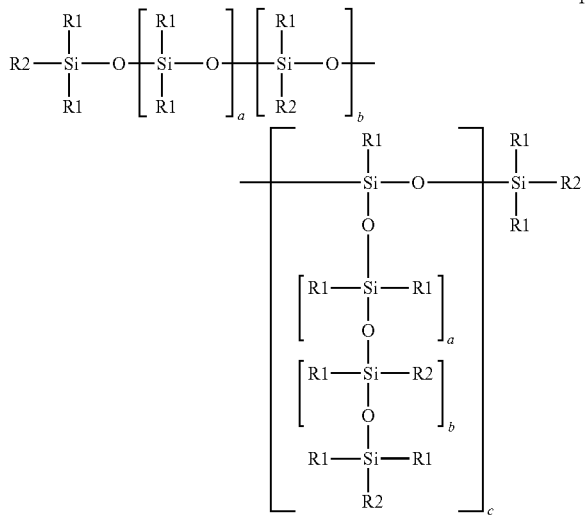

in which
$R^1$ are identical or different aliphatic or aromatic hydrocarbon radicals having 1 to 20 carbon atoms,
$R^2$ is $R^1$ or H, with the proviso that at least three radicals $R^2$ are H,
a is 5 to 500,
b is 1 to 50,
c is 0 to 5,
onto a siloxane of general formula II containing double bonds

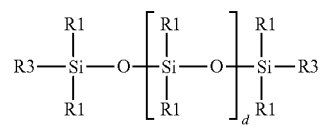

where
d is 10 to 1000 and $R^3$, independently of one another, are identical or different hydrocarbon radicals having 2 to 12 carbon atoms and containing at least one double bond, wherein said incorporating includes an addition reaction of said at least one organopolysiloxane of general formula I onto said siloxane of general formula II in the presence of a platinum catalyst or a rhodium catalyst, with the proviso that at least one organopolysiloxane of the general formula I is present in at least a 6-fold molar excess, based on the siloxane of the general formula II containing double bonds, to give a reaction product having Si—H groups; and
reacting the reaction product in at least one of the stages of:

B) a transition-metal-catalysed partial or complete addition of the SiH groups onto alkenyl and/or alkynyl compounds, or C) a partial or complete reaction of the Si—H groups remaining after the above reaction(s) in the presence of a catalyst with at least one alcohol selected from the group of linear or branched, saturated, mono- or poly-unsaturated, aromatic, aliphatic-aromatic, optionally halogen-atom-containing monoalcohols, polyether monoalcohols, polyester monoalcohols, and amino alcohols.

2. The method according to claim 1, wherein each $R^1$ is an identical or different unbranched, aliphatic or aromatic hydrocarbon radical having 1 to 9 carbon atoms.

3. The method according to claim 1, wherein in stage B), the addition is onto a polyether containing a double bond.

4. The method according to claim 1, wherein in stage B) the addition is onto an allyl polyether.

5. The method according to claim 1, wherein a boron-containing Lewis acid is used as the catalyst in stage C).

6. The method according to claim 5, wherein said boron-containing Lewis acid is tris(pentafluorotriphenylborane) $(C_5F_4)_3B$.

7. The method according to claim 5, wherein stage C) further comprises co-use of a synergistically effective compound.

8. The method according to claim 7, wherein said synergistically effective compound is a salt or a complex with cations selected from the group of salts of elements of the 4th, 6th, 7th and 8th subgroup and of the 4th main group of the Periodic Table of Elements.

9. The method according to claim 1, wherein a catalytic mixture comprising at least one carboxylic acid and at least one salt of a carboxylic acid is used as the catalyst in stage C).

10. The method according to claim 1, wherein the organomodified siloxane block copolymer has a visocosity of <10,000 mPas.

11. A method of treating human or animal body parts comprising applying the organomodified siloxane block copolymer prepared by the method recited in claim 1 to at least one human or animal body part requiring treatment.

12. The method according to claim 11, wherein said organomodified siloxane block copolymer is in a form of an emulsion, a suspension, a solution, a cream, an ointment, a paste, a gel, an oil, a powder, an aerosol, a stick, a spray, a cleansing product, a make-up or sunscreen preparation or a facial toner.

13. The method according to claim 11 wherein said at least one human or animal body part includes skin and/or hair.

14. An organomodified siloxane block copolymer prepared in according to claim 1, wherein said organomodified siloxane block copolymer has a viscosity of less than 10,000 mPas.

15. A formulation for the care of human or animal body parts, said formulation is an aqueous surface-active formulation comprising, water, an emulsifier, a surfactant, a cosmetic oil component, and as a care active ingredient, an organomodified siloxane block copolymer prepared according to the method of claim 1, wherein said aqueous surface-active formulation based on total mass, comprises less mass percent of said oil component than a sum of mass percents of said emulsifier and said surfactant.

16. The formulation according to claim 15, wherein said organomodified siloxane block copolymer comprises from 0.01 mass percent to 20 mass percent of care active ingredient, based on the total mass of the formulation.

17. The formulation according to claim 15, further comprising at least one additional component selected from the group of
- thickeners/viscosity regulators/stabilizers,
- UV photoprotective filters,
- antioxidants,
- hydrotropes or polyols,
- solids and fillers,
- film-formers,
- pearlescent additives,
- deodorant and antiperspirant active ingredients,
- insect repellents,
- self-tanning agents,
- preservatives,
- conditioners,
- perfumes,
- dyes,
- cosmetic active ingredients,
- care additives,
- superfatting agents, and
- solvents.

18. The formulation of claim 15, wherein said aqueous surface-active formulation comprises, based on the total mass of the formulation, at least 20 mass percent of said water.

19. The formulation of claim 15, wherein said aqueous surface-active formulation comprises, based on the total mass of the formulation, at least 0.01 mass percent of said care active ingredient.

20. The formulation of claim 15, wherein said aqueous surface-active formulation comprises, based on the total mass of the formulation, from 0.1 mass percent to 3 mass percent of said care active ingredient.

* * * * *